United States Patent
Shioda et al.

(10) Patent No.: US 6,251,676 B1
(45) Date of Patent: Jun. 26, 2001

(54) MAMMALIAN CELL TWO-HYBRID SYSTEM

(75) Inventors: Toshihiro Shioda, Burlington; Kurt J. Isselbacher, Newton, both of MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 09/534,060

(22) Filed: Mar. 24, 2000

(51) Int. Cl.[7] .............................. C12N 15/63; C12N 5/00; C12N 15/00; C12Q 1/68; C12P 19/34

(52) U.S. Cl. .......................... 435/455; 435/6; 435/91.1; 435/325; 435/320.1

(58) Field of Search ............................ 435/6, 91.1, 91.2, 435/183, 69.1, 455, 463, 465, 476, 325, 252.3, 254.2, 320.1, 810; 436/94, 501; 536/23.1, 24.3, 24.33, 25.3

(56) References Cited

U.S. PATENT DOCUMENTS 6,114,111    9/2000   Luo et al. .

OTHER PUBLICATIONS

James B. Allen, Mark W. Walberg, Michael C. Edwards, and Stephen J. Elledge, "Finding prospective partners in the library: the two–hybrid system and phage display find a match," Tibs 20, Dec. 1995, pp. 511–515.

Eric R. Fearon, Toren Finkel, Maura L. Gillison, Scott P. Kennedy, James F. Casella, Gordon F. Tomaselli, Jon S. Morrow, and Chi Van Dang, "Karyoplasmic interaction selection strategy: A general strategy to detect protein–protein interactions in mammalian cells," Proceedings of the National Academy of Science USA, vol. 89, Sep. 1992, pp. 7958–7962.

Sharon Naik, Jayashree M. Paranjape, and Robert H. Silverman, "RNase L dimerization in a mammalian two–hybrid system in response to 2',5'–oligoadenylates," Nucleic Acids Research, vol. 26, No. 6, 1998, pp. 1522–1527.

Adrienne M. Takacs, Tapas Das, and Amiya K. Banerjee, "Mapping of interacting domains between the nucleocapsid protein and the phosphoprotein of vesicular stomatitis virus by using a two–hybrid system," Proceedings of the National Academy of Science USA, vol. 90, Nov. 1993, pp. 10375–10379.

Haren A. Vasvada, Subinay Ganguly, F. Joseph Germino, Zhen Xi Wang, and Sherman M. Weissman, "A contingent replication assay for the detection of protein–protein interactions in animal cells," Proceedings of the National Academy of Science USA, vol. 88, Dec. 1991, pp. 10686–10690.

(List continued on next page.)

Primary Examiner—Ethan Whisenant
Assistant Examiner—Frank Lu
(74) Attorney, Agent, or Firm—Fish & Richardson P.C.

(57) ABSTRACT

The invention provides a method of using a reporter gene that encodes a fluorescent polypeptide to indicate that an interaction has occurred between a bait and a prey protein in a mammalian cell. An advantage of using a fluorescent reporter polypeptide is that an interaction between a bait and prey in a mammalian cell can be readily detected, e.g., within 96 hours. In another method of the invention, a prey plasmid contains an Epstein-Barr virus origin of replication (ori-P). The OriP permits the prey plasmid to replicate episomally and indefinitely without damaging the mammalian cell or integrating into the genomic DNA of the mammalian cell. Since such a plasmid is maintained episomally in a circular form, it can be readily recovered from the mammalian cell.

7 Claims, 7 Drawing Sheets

OTHER PUBLICATIONS

Cormack et al., Isolation of putative plant transcriptional coactivators using a modified two–hybrid system incorporating a GFP reporter gene. The Plant Journal 14, 685–692, Jun. 1998.*

Tanaka et al., Construction of Epstein–Barr Virus–based expression vector containing mini–oriP. Biochem. Biophys. Res. Commun. 264, 938–943, Nov. 1999.*

Mazda et al., Extremely efficient gene transfection into lympho–hematopoietic cell lines by Epstein–Barr Virus-based vectors. J. Immun. Methods 204, 143–151, May 1997.*

Krafte et al., Stable expression and functional characterization of a human cardiac Na+ channel genes in mammalian cells. J. Mol. Cell Cardiol. 27, 823–830, Feb. 1995.*

* cited by examiner

MAMMALIAN CELL TWO-HYBRID SYSTEM

FIELD OF THE INVENTION

This invention relates to molecular biology.

BACKGROUND OF THE INVENTION

One approach for elucidating protein-protein binding in cells is the yeast-based two-hybrid system (Fields and Song (1989) Nature 340:245). That system utilizes chimeric genes and detects protein-protein interactions via the activation of reporter-gene expression. Reporter-gene expression occurs as a result of reconstitution of a functional transcription factor caused by the association of fusion proteins encoded by the chimeric genes. Typically, polynucleotides encoding two-hybrid proteins are constructed and introduced into a yeast host cell. The first hybrid protein consists of the yeast Gal4 DNA-binding domain fused to a polypeptide sequence of a known protein (often referred to as the "bait"). The second hybrid protein consists of the Gal4 activation domain fused to a polypeptide sequence of a second protein (often referred to as the "prey"). Binding between the two-hybrid proteins reconstitutes the Gal4 DNA-binding domain with the Gal4 activation domain, which leads to the transcriptional activation of a reporter gene (e.g., lacZ or HIS3), which is operably linked to a Gal4 binding site.

SUMMARY OF THE INVENTION

In a first method, expression of a reporter gene that encodes a fluorescent polypeptide is used to indicate that an interaction has occurred between a bait and a prey protein. An advantage of using a fluorescent reporter polypeptide is that an interaction between a bait and prey in a mammalian cell can be readily detected, e.g., within 96 hours. In addition, the use of a fluorescent reporter polypeptide allows the identification of a single fluorescing mammalian cell without further manipulation or damage to the cell. For example, a cell that fluoresces can be identified under a fluorescent microscope. To determine the sequence of the prey protein, total DNA from a fluorescing cell is prepared, and the DNA sequence that encodes the prey amplified and sequenced.

In a second method, a prey plasmid containing an Epstein-Barr virus origin of replication (ori-P) and a bait plasmid are transfected into a mammalian cell that expresses Epstein-Barr virus nuclear antigen-1 (EBNA-1). The oriP allows the prey plasmid to replicate episomally and indefinitely in the cell. Since the prey plasmid is maintained episomally in a closed circular form, the prey plasmid can be readily introduced and recovered from a bacterial host cell.

In one aspect, the invention features a method for detecting an interaction between a bait and a prey in a mammalian cell. The method includes: (a) providing a mammalian cell containing: (i) a reporter gene encoding a fluorescent polypeptide operably linked to a transcriptional regulatory sequence containing a DNA binding site for a DNA-binding domain, (ii) a bait nucleotide sequence encoding a bait fusion protein, including a DNA binding domain and the bait; (iii) a prey nucleotide sequence encoding a prey fusion protein including a transcriptional activation domain and a prey; (b) incubating the cell for 96 hours or less; e.g., 72, 48, 24, or 16 hours; (c) detecting reporter gene expression, if present, thereby detecting an interaction between the bait and the prey.

The method can further include isolating total DNA from a cell expressing the reporter gene, and amplifying the nucleotide sequence that encodes the bait or prey. In one embodiment, the reporter gene is integrated into a chromosome of the cell. In another embodiment, the bait or prey is encoded by a nucleotide sequence from a nucleic acid library. The cell can be any mammalian cell, e.g., a primary, secondary or an immortalized cell such as a CV-1 cell. The reporter gene can be a fluorescent polypeptide such as a green fluorescent protein (GFP) or a blue fluorescent protein (BFP).

In another aspect, the invention features a method for detecting an interaction between a bait and a prey in a mammalian cell. The method includes: (a) providing a mammalian cell containing (i) an Epstein-Barr virus nuclear antigen-1 (EBNA-1); (ii) a reporter gene operably linked to a transcriptional regulatory sequence containing a DNA binding site for a DNA-binding domain, (iii) a bait nucleotide sequence encoding a bait fusion protein, including a DNA-binding domain and the bait (e.g., a known protein), (iv) a prey nucleotide sequence including an origin of replication for the Epstein-Barr virus nuclear antigen-1 (oriP) and encoding a prey fusion protein including a transcriptional activation moiety and the prey (e.g., an unknown protein); and (b) detecting reporter gene expression, if present, thereby detecting an interaction between the bait and the prey. The method can further include (c) isolating DNA from a cell expressing the reporter gene; and (d) recovering the nucleotide sequence including the oriP sequence, which encodes the prey fusion protein. An example of a suitable reporter gene includes a reporter gene that encodes a fluorescent protein such as a green fluorescent protein or a blue fluorescent protein. In some embodiments, the reporter gene is integrated into a chromosome of the cell. The cell can be any mammalian cell that expresses EBNA-1 (or manipulated to express EBNA-1). An example of a mammalian cell includes a cell derived from a primate or a canine. The cell can be a primary, secondary or an immortalized cell. An example of an immortalized cell is a CV-1 cell. The bait and/or the prey can be encoded by a nucleotide sequence from a nucleic acid library.

The invention also features a kit for detecting an interaction between a bait and prey in a mammalian cell. The kit includes: (a) a first gene construct which includes a regulatory sequence operably linked to a nucleotide sequence encoding a DNA-binding domain, and wherein the first gene construct includes a cloning site for inserting a nucleotide sequence encoding the bait into the first gene construct such that the bait is expressed in frame with the DNA-binding domain; (b) a second gene construct which includes: an oriP sequence, a regulatory sequence operably linked to a nucleotide sequence encoding a transcriptional activation domain, and wherein the second gene construct includes a cloning site for inserting a nucleotide sequence encoding the prey into the second gene construct such that the prey is expressed in frame with the transcriptional activation domain; (c) a mammalian cell that expresses an EBNA-1, including a reporter gene encoding a fluorescent polypeptide operably linked to a transcriptional regulatory sequence including a DNA binding site for the DNA-binding domain, wherein the reporter gene expresses the fluorescent polypeptide when the bait and prey interact; and (d) instructions for use.

Also within the scope of the invention is a method of identifying an agent that disrupts interaction between a bait and a prey, including: (a) providing a mammalian cell having: (i) a reporter gene encoding a fluorescent polypeptide operably linked to a transcriptional regulatory sequence including a DNA binding site for a DNA-binding domain, (ii) a first nucleotide sequence encoding a bait fusion protein, including a DNA-binding domain and the bait, (iii) a second nucleotide sequence encoding a prey fusion protein including a transcriptional activation domain and the prey; (b) contacting the mammalian cell with a test agent; (c) incubating the cell for 96 hours or less, e.g., 72, 48, 24 or 16 hours; and (d) detecting a decrease in expression of the reporter gene compared to the level of expression of the reporter gene in a mammalian control cell, if present, thereby detecting an agent that disrupts interaction between the bait and the prey.

The invention further features a method of identifying an agent that enhances interaction between a bait and a prey, including: (a) providing a mammalian cell having: (i) a reporter gene encoding a fluorescent polypeptide operably linked to a transcriptional regulatory sequence including a DNA binding site for a DNA-binding domain, (ii) a bait nucleotide sequence encoding a bait fusion protein including a DNA-binding domain and the bait, (iii) a prey nucleotide sequence encoding a prey fusion protein including a transcriptional activation domain and a prey; (b) incubating the cell for a period of time, e.g., 96 hours or less e.g., 78, 48, 24, or 16 hours; and (c) detecting an increase in expression of the reporter gene compared to the level of expression of the reporter gene in a mammalian control cell, thereby detecting an agent that disrupts interaction between the bait and the prey.

As used herein, "DNA-binding domain" means an amino acid sequence that binds specifically to a particular DNA sequence. The site where the DNA-binding domain binds is known as a DNA binding site.

As used herein, "transcriptional activation domain" means an amino acid sequence which when in proximity to transcriptional regulatory DNA elements of a target gene, activates gene transcription.

As used herein, a "reporter gene" means a gene whose expression can be assayed.

As used herein, "interactor" means a protein which is able to form a complex with another protein.

Unless otherwise defined, all technical and scientific terms used herein have the same meaning as commonly understood by one of ordinary skill in the art to which this invention belongs. In case of conflict, the present application, including definitions will control. All publications, patent applications, patents and other references mentioned herein are incorporated by reference.

Although methods and materials similar or equivalent to those described herein can be used in the practice or testing of the invention, preferred methods and materials are described below. The materials, methods, and examples are illustrative only and not intended to be limiting. Other features and advantages of the invention will be apparent from the detailed description and the claims.

DETAILED DESCRIPTION

Figure 1:
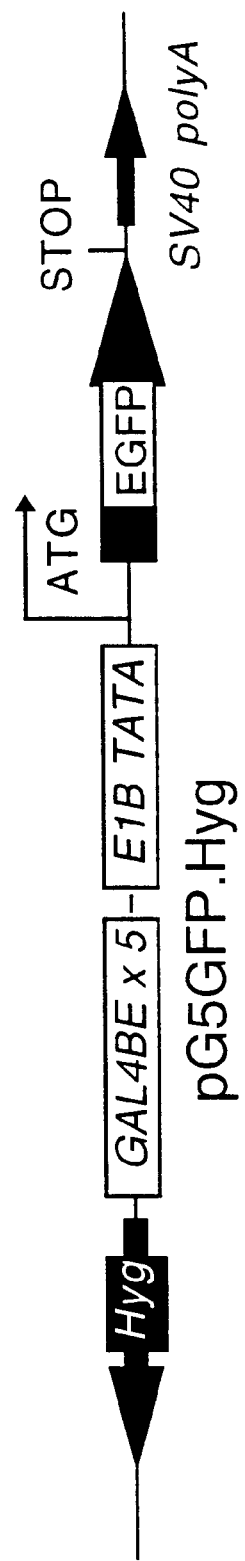
FIG. 1 is a schematic drawing of the GAL4-dependent GFP reporter plasmid, pG5GFP.Hyg.
Figure 2:
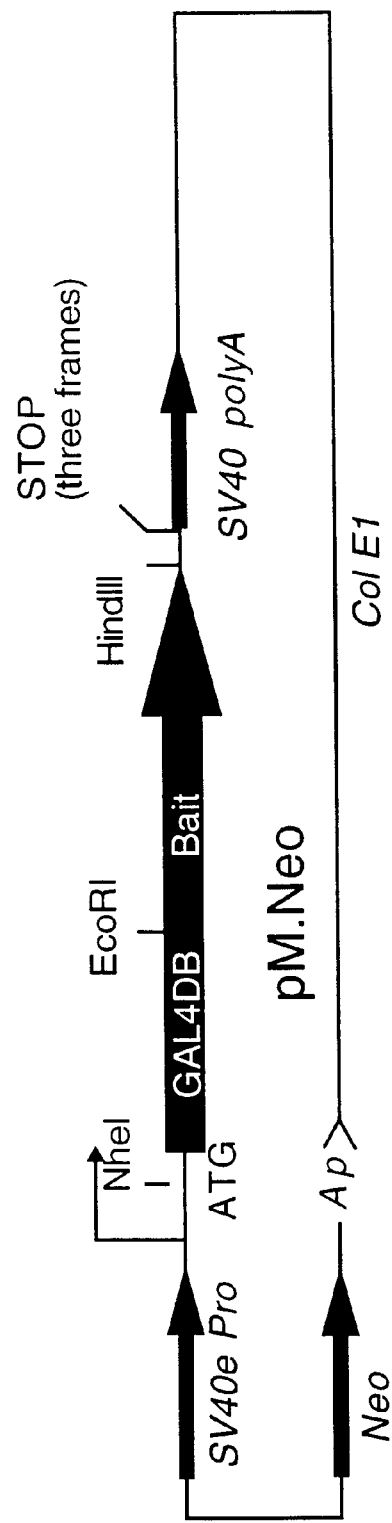
FIG. 2 is a schematic drawing of a bait expression plasmid, pM.Neo. Also depicted are the unique restriction site(s), EcoR1 and HindIII, for inserting a bait nucleotide sequence, the GAL4 DNA-binding domain (GAL4BD), SV40 early promoter (SV40e), and the selection marker neomycin (Neo).

In one method, a mammalian host cell is engineered such that an interaction between the bait protein and the prey protein results in expression of a reporter gene which encodes a fluorescent protein. The cell in which the prey and bait interact is referred to as a "positive" cell. Cells that fluoresce can be readily detected, e.g., under a fluorescent microscope, as early as 16 hours after transfection, and the prey sequence amplified and identified. The advantage of using a fluorescent protein as a reporter is that single fluorescent cells can be readily identified without damaging the cells and without further manipulation. For example, the present method overcomes the need for identifying positive cells based on expression of a drug selectable marker gene. Drug selection (e.g., G418 or hygromycin B) usually requires too much time for a single screening and the conditions (drug concentration and selection period) have to be optimized empirically.

In another method, a prey plasmid containing an Epstein-Barr virus origin of replication (ori-P) and a bait plasmid are transfected into a mammalian cell that expresses Epstein-Barr virus nuclear antigen-1 (EBNA-1). OriP permits the prey plasmid to replicate episomally and indefinitely without damaging the mammalian cell or integrating into the genomic DNA of the mammalian cell. Since such a plasmid is maintained episomally in a circular form, it can be readily introduced and recovered from a bacterial host. The advantage of using an oriP prey plasmid is that the use of this plasmid overcomes degradation problems associated with transient transfection. Normally, transiently introduced plasmids are degraded within several days in mammalian cells if there is no specific mechanism to maintain them. This period (usually 2 to 3 days) is not long enough to isolate and purify single cell-derived colonies expressing the positive prey genes. This is a practical limitation on the efficient isolation of the true positive clones. The present system overcomes this limitation.

It will be appreciated by those skilled in the art that many variations of the prey and bait fusion proteins can be constructed and is considered within the scope of the present invention. For example, it will be understood that, for screening polypeptide libraries, the library can be cloned into either the bait or prey fusion proteins. In this sense, the terms "prey" and "bait" are merely convenient names for fusion proteins with transcriptional activation domains and DNA-binding domains, respectively.

Each component of the system is now described in more detail.

Bait Protein

The bait fusion protein includes a fusion between a polypeptide moiety of interest (e.g., a protein of interest or a polypeptide from a polypeptide library), and a DNA-binding domain which specifically binds a DNA binding site which occurs upstream of an appropriate reporter gene. The nucleotide sequence which encodes the polypeptide moiety of interest is cloned in-frame to a nucleotide sequence encoding the DNA-binding domain.

Any polypeptide that binds a defined DNA sequence can be used as a DNA-binding domain. The DNA-binding domain can be derived from a naturally occurring DNA-binding protein, e.g., a prokaryotic or eukaryotic DNA-binding protein. Alternatively, the DNA-binding domain can be a polypeptide derived from a protein artificially engineered to interact with specific DNA sequences. Examples of DNA-binding domains from naturally occurring eukaryotic DNA-binding proteins include p53, Jun, Fos, GCN4, or GAL4. The DNA-binding domain of the bait fusion protein can also be generated from viral proteins, such as the pappillomavirus E2 protein. In another example, the DNA-binding domain is derived from a prokaryote, e.g., the E. coli LexA repressor can be used, or the DNA-binding domain can be from a bacteriophage, e.g., a lambda cI protein. Exemplary prokaryotic DNA-binding domains include DNA-binding portions of the P22 Arc repressor, MetJ, CENP-B, Rap1, Xy1S/Ada/AraC, Bir5 and DtxR.

The DNA-binding protein also can be a non-naturally occurring DNA-binding domain and can be generated by combinatorial mutagenic techniques. Methods for generating novel DNA-binding proteins which can selectively bind to a specific DNA sequence are known in the art. See e.g., U.S. Pat. No. 5,198,346.

The basic requirements of the bait fusion protein include the ability to specifically bind a defined nucleotide sequence (i.e., a DNA binding site) upstream of the appropriate reporter gene. The bait fusion protein should cause little or no transcriptional activation of the reporter gene in the absence of an interacting prey fusion protein. It is also desirable that the bait not interfere with the ability of the DNA-binding domain to bind to its DNA binding site.

As appropriate, the DNA-binding domain used in the bait fusion protein can include oligomerization motifs. It is known in the art that certain transcriptional regulators dimerize. Dimerization promotes cooperative binding of the transcriptional regulators to their cognate DNA binding sites. For example, where the bait protein includes a LexA DNA-binding domain, it can further include a LexA dimerization domain; this optional domain facilitates efficient LexA dimer formation. Because LexA binds its DNA binding site as a dimer, inclusion of this domain in the bait protein also optimizes the efficiency of binding (Golemis and Brent, (1992) Mol. Cell Biol. 12:3006). Other exemplary motifs include the tetramerization domain of p53 and the tetramerization domain of BCR-ABL.

The bait portion of the bait fusion protein may be chosen from any protein of interest and includes proteins of unknown, known, or suspected diagnostic, therapeutic, or pharmacological importance. For example, the protein of interest can be a protein suspected of being an inhibitor or an activator of a cellular process (e.g., receptor signaling, apoptosis, cell proliferation, cell differentiation, or import or export of toxins and nutrients). Examples of bait proteins include oncoproteins such as myc, Ras, Src, Fos; tumor-suppressor proteins such as p53, p21, p16, Rb, and constitutively active Rb with deleted phosphorylation sites; (Knudsen et. al., Oncogene, 1999, 18:5239–45); proteins involved in cell-cycle regulation such as kinases and phosphates; or proteins involved in signal transduction, e.g., T-cell signaling, e.g., Zap-70 or SAM-68. The full length of the protein of interest, or a portion thereof, can be used as the bait protein. In the instance when the protein of interest is of a large size, e.g., has a molecular weight of over 20 kDa, it may be more convenient to use a portion of the protein.

DNA sequences which encode for the polypeptide of interest and the DNA-binding domain, e.g., the nucleic acid sequence which encodes for the GAL4 DNA-binding domain, are inserted into a vector such that the desired bait fusion protein is produced in a host mammalian cell. Suitable recombinant expression vectors are known in the art, e.g., pSG424 (Sadowski and Ptashne, Nucleic Acid Research, 17:7539, 1989), or pM (Clontech, Palo Alto, Calif.). Preferably the recombinant expression vector includes one or more regulatory sequences operably linked to the fusion nucleic acid sequence to be expressed. The term "regulatory sequence" includes promoters, enhancers and other expression control elements (e.g., polyadenylation signals) and these sequences direct expression of the fusion protein.

Optionally, the vector can also include a selectable marker, the expression of which in the host mammalian cell permits selection of cells containing the marker gene from cells that do not contain the marker gene. Selectable markers are known in the art, e.g., neomycin, zeocin or blasticidin.

Figure 3:
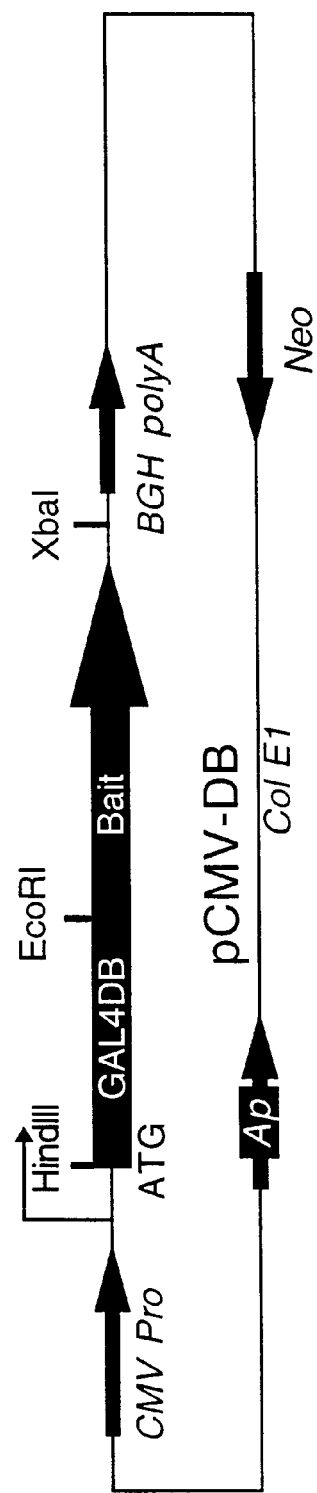
FIG. 3 is a schematic drawing of a bait expression plasmid, pCMV-DB. Also depicted are the unique restriction site(s), EcoR1 and XbaI, for inserting a bait nucleotide sequence, the GAL4 DNA-binding domain (GAL4BD), a CMV promoter, and the selection marker neomycin (Neo).
Figure 4:
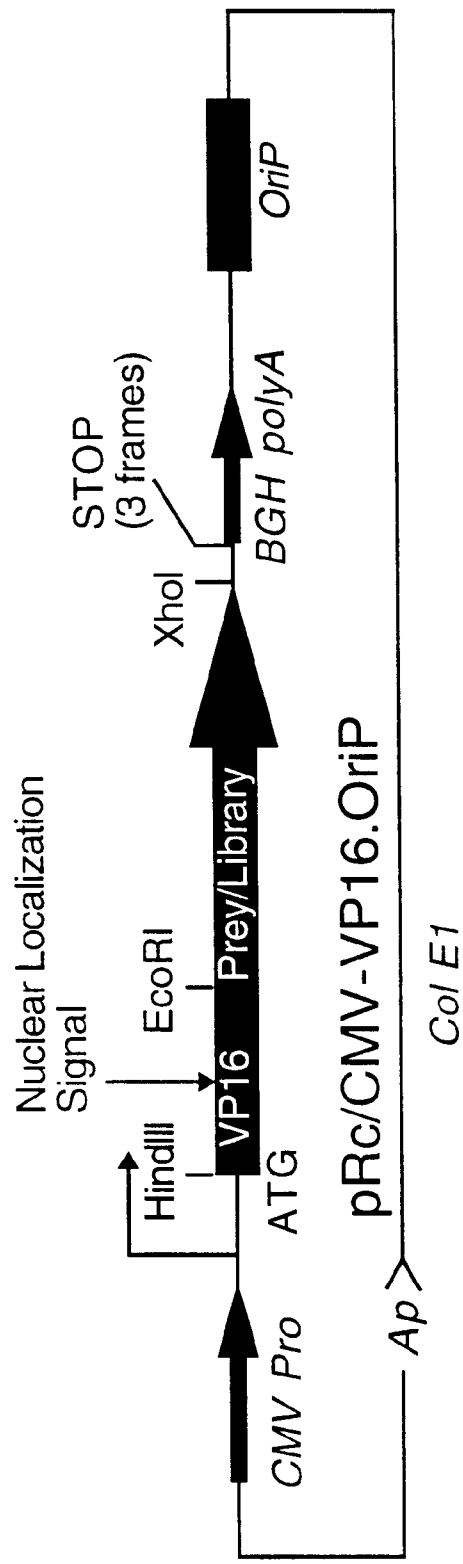
FIG. 4 is a schematic drawing of a prey plasmid, pRc/CMV-VP16.OriP. Also depicted are the unique restriction site(s), EcoR1 and XhoI, for inserting a prey nucleotide sequence, the VP16 activation domain (VP16), the origin of replication, oriP, and the selection marker ampicillin (Ap).

Exemplary bait plasmids are shown in FIGS. 3 and 4. To construct the bait plasmid shown in FIG. 3, pM.Neo, a cDNA of interest can be subcloned into the vector pM (available from Clontech, Palo Alto, Calif.) at the unique EcoR1 and HindIII sites in frame to the N-terminal GAL4 DNA-binding domain (GAL4DB). Alternatively, the pCMV-DB bait plasmid shown in FIG. 4 can be constructed by exising the GAL4 DNA-binding domain cDNA from pSG424 (HindIII-EcoR1 fragment) and inserting the fragment into the HindIII/EcoR1 site within the multiple cloning site of the vector pcDNA3 (available from Invitrogen, Carlsbad, Calif.). The bait insert can be cloned into the unique EcoR1/XbaI site. Expressed mRNA is stabilized by the bovine growth hormone (BGH) polyadenylation sequence.

Preferably, the vector is integrated into a chromosome of the cell.

It may also be preferable to introduce an unstructured polypeptide linker region between the DNA-binding domain of the fusion protein and the bait polypeptide sequence. The linker can facilitate, e.g., enhanced flexibility of the fusion protein allowing the DNA-binding domain to freely interact with the DNA binding site.

Prey Fusion Protein

Figure 7:
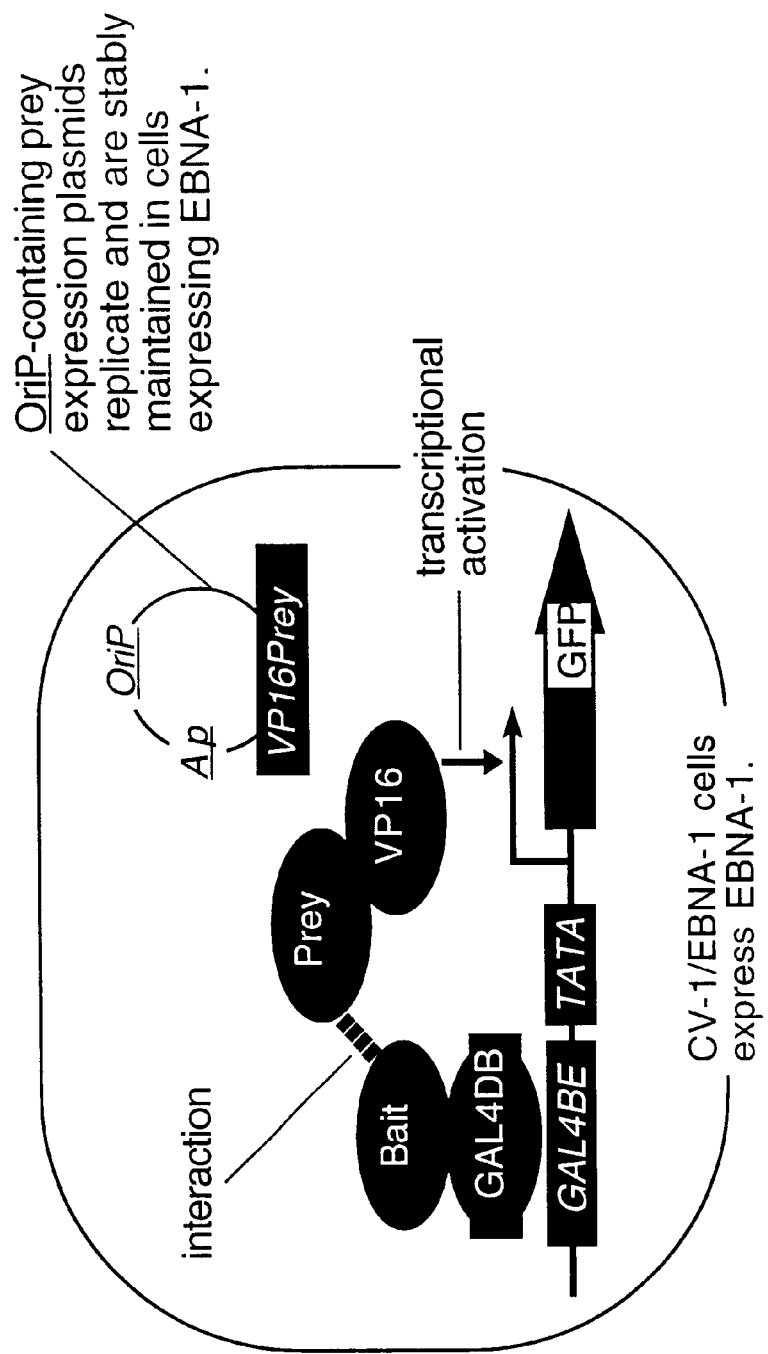
FIG. 7 is a schematic drawing depicting a bait-prey interaction.

The prey fusion protein includes a transcriptional activation domain and a candidate interactor polypeptide sequence which is to be tested for its ability to form an intermolecular association with the bait polypeptide. As discussed above, protein-protein contact between the bait and prey fusion proteins (via the interaction of the bait and prey polypeptide portions of these proteins) links the DNA-binding domain of the bait fusion protein with the activation domain of the prey fusion protein, generating a protein complex capable of directly activating expression of the reporter gene (see FIG. 7).

Any of a number of activation domains can be used in the prey fusion protein. The activation domain can be a naturally occurring activation domain, e.g., an activation domain that is derived from a eukaryotic or prokaryotic source. Exemplary activation domains include GAL4, VP16, CR2, B112, or B117. The activation domain can also be derived from a virus, e.g., VP16 activation domain is derived from herpesvirus.

DNA sequences which encode the prey and the transcriptional activation domain, e.g., a VP16 activation domain, can also include other sequences such as a nuclear localization sequence (e.g., those derived from GAL4 or MAT.alpha.2.genes). The nuclear localization sequence optimizes the efficiency with which prey proteins reach the nuclear-localized reporter gene construct.

The prey polypeptide can be any polypeptide, e.g., the prey polypeptide can be derived from all or a portion of a known protein or a mutant thereof, all or a portion of an unknown protein (e.g., encoded by a gene cloned from a cDNA library), or a random polypeptide sequence.

To isolate DNA sequences encoding novel interacting proteins, members of a DNA expression library (e.g., a cDNA or synthetic DNA library) can be fused in-frame to the transcriptional activation domain to generate a variegated library of prey fusion proteins.

In an exemplary embodiment, a cDNA library may be constructed from an mRNA population and inserted into an expression vector. Such a library of choice may be constructed de novo using commercially available kits (e.g., from Stratagene, La Jolla, Calif.) or using well established preparative procedures (see, for example, Current Protocols in Molecular Biology, Eds. Ausubel et al. John Wiley & Sons: 1992). Alternatively, a number of cDNA libraries (from a number of different organisms) are publicly and commercially available; sources of libraries include, e.g., Clontech (Palo Alto, Calif.) and Stratagene (La Jolla, Calif.). It is also noted that prey polypeptides need not be naturally occurring full-length proteins. In certain embodiments, prey proteins can be encoded by synthetic DNA sequences.

DNA sequences which encode for the prey protein and the activation domain, e.g., the nucleic acid sequence which encodes for the VP-16 activation domain, are inserted into a vector such that the desired prey fusion protein is produced in a host mammalian cell. The vector can be any expression vector as described above. In the instance where it is preferable to recover the prey sequence using a bacterial host cell, as described above, the prey DNA sequences are inserted into a vector which contains an appropriate origin of replication. By an appropriate origin of replication is meant an origin of replication which allows the vector to be maintained episomally and indefinitely without damaging the mammalian host cell or integrating the DNA sequence into the genomic DNA of the mammalian host cell. Since the vector is maintained episomally, the vector can be easily introduced and recovered from a bacterial host cell. An example of such a suitable origin of replication is the oriP EpsteinBarr virus replication origin sequence (oriP). In a preferred embodiment, a vector containing an oriP is transformed into a mammalian cell which contains an Epstein Barr virus nuclear antigen-1 (EBNA-1). A vector containing an oriP can replicate stably in a mammalian cell that expresses EBNA-1 (Aiyar et al., EMBO Journal, 17:12:6394–6403).

Figure 5:
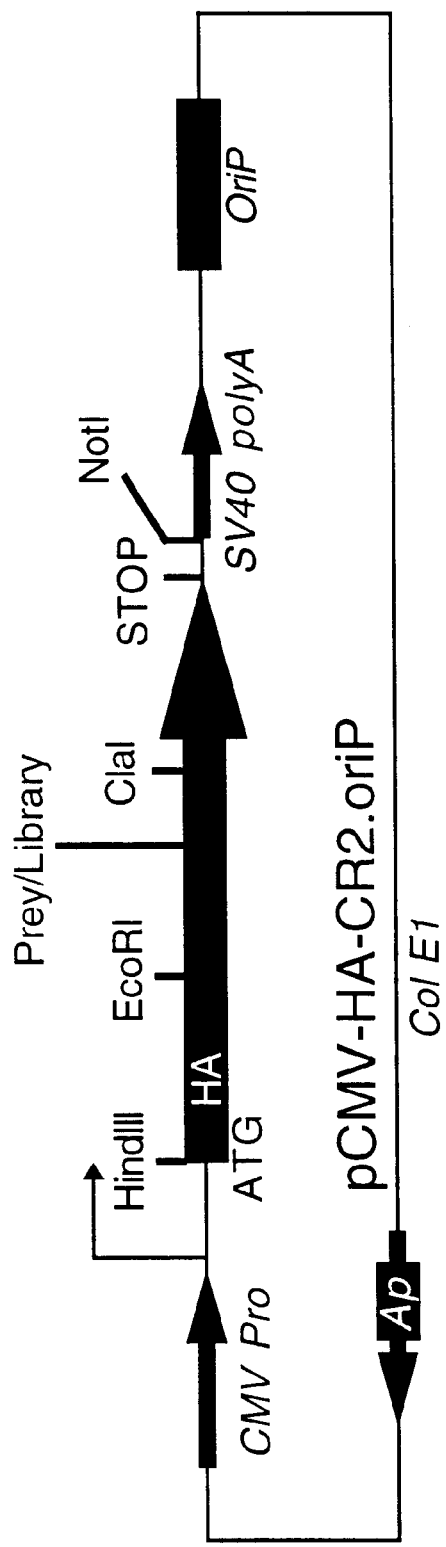
FIG. 5 is a schematic drawing of a prey plasmid, pCMV-HA-CR2.ori-P. Also depicted are the unique restriction site(s), EcoR1 and ClaI, for inserting a prey nucleotide sequence, the CR2 activation domain (CR2), the origin of replication, oriP, the CMV promoter and the selection marker ampicillin (Ap).

Exemplary prey plasmids are shown in FIGS. 4 and 5. The prey plasmid of FIG. 4, pRc/CMV-VP16.OriP, can be constructed by subcloning a prey into the unique EcoRI and XhoI sites of the pCEP4 vector (Invitrogen, Carlsbad, Calif.) to generate fusion proteins with the herpesvirus VP16 transactivator domain harboring an SV40 nuclear localization signal sequence. Alternatively, the pCMV-HA-CR2.oriP plasmid can be constructed by removing the EBNA-1 expression cassette and the hygromycin resistant gene expression cassette from pCEP4 (Invitrogen, Carlsbad, Calif.). An expression cassette of a HA-tagged prey can be inserted into the HinDIII/NotI sites within the multiple cloning site of the pCEP4 vector. This plasmid harbours the oriP sequence derived from pCEP4.

Additional Variations of the Prey and Bait Fusion Proteins

In another aspect of the present invention, the DNA sequence encoding the prey protein (or alternatively the bait protein) is embedded in a DNA sequence encoding a conformation-constraining protein (i.e., a protein that decreases the flexibility of the amino and carboxy termini of the prey protein). This improves the stability of the fusion protein structure. Such embodiments are preferred where the prey polypeptide is a relatively short peptide, e.g., 5–25 amino acid residues. In general, conformation-constraining proteins act as scaffolds or platforms, which limit the number of possible three-dimensional configurations the peptide or protein of interest is free to adopt. Examples of conformation-constraining proteins are thioredoxin or other thioredoxin-like sequences, but many other proteins are also useful for this purpose.

Reporter Gene

Expression of the reporter gene indicates an interaction between the prey and bait polypeptides, and permits the identification of mammalian cells in which an interaction has occurred. The reporter gene sequence will include a reporter gene operably linked to a DNA binding site to which the DNA-binding domain of the bait fusion protein binds.

In a preferred embodiment of the invention, the reporter gene encodes a fluorescent molecule, e.g., a green fluorescent protein (GFP) or a blue fluorescent protein (BFP). The advantage of using a reporter gene that encodes a fluorescent protein is that a single individual fluorescent positive cell can be identified quickly. For example, using GFP as the reporter gene product, green fluorescence can be detected as early as 16 hours after transfection. Positive (fluorescent) cells can be identified using a fluorescence microscope, .e.g., using an inverted phase-contrast microscope equipped with an epifluorescence light source and a fluorescein isothiocyanate filter set. Using this method, positive cells can be identified without damage to the cells, e.g., positive, green fluorescent cells can be easily isolated by conventional cell cloning methods, such as using small plastic cylinders to isolate cells, or collecting positive cells directly using a conventional micropipette (such as Gilson Pipettman). Alternatively, floursesence-activated cell sorter (FACS) can be used to isolate positive cells. However, isolating positive cells by FACS is less preferable, since this approach will mix up the positive clones, and hence, may cause cloning bias. The total DNA from a positive clone can be prepared by standard procedures and the sequence which encodes the prey protein amplified using PCR and sequenced by standard procedures.

A preferred fluorescent polypeptide is derived from a GFP. The GFP gene was originally cloned from the jellyfish *Aequorea victoria*. It encodes a protein of 238 amino acids which absorbs blue light (major peak at 395 nm) and emits green light (major peak at 509 nm) (Prasher et al., *Gene* 15:229–223, 1992). GPF genes and functional proteins have been identified in a variety of organisms in the phyla hydrozoa, cnidaria, anthozoa and ctenophora. Both wild-type GFP and mutated GFP from *Aequorea victoria* can be used as a reporter gene. The mutation of GFP (e.g., the substitution of certain amino acids in the GFP polypeptide)

has been reported to yield GFP proteins with improved spectral properties. For example, mutating serine 65 to a threonine generates a GFP variant which has about sixfold greater brightness than wild-type GFP (Heim et al., *Nature* 372:663–664, 1995). The coding sequence for an enhanced GFP can be purchased commercially (Clontech, Palo Alto, Calif.). In some embodiments a mammalian-optimized version of a GFP cDNA is used.

BPF can also be used as a reporter gene. To obtain BFP, tyrosine 66 of GFP is mutated to a histidine. This mutated GFP protein fluoresces bright blue, in contrast to the green of the wild-type protein. Other variants of GFP include yellow fluorescent protein (YFP), and cyan fluorescent protein (CFP). Other suitable fluorescent proteins include those described by Matz et al., 1999, Nature Biotechnology 17:969–973.

In the second aspect of the invention, any suitable reporter gene can be used. Examples include chloramphenicol acetyl transferase (CAT; Alton and Vapnek (1979), Nature 282:864–869), and other enzyme detection systems, such as beta-galactosidase; firefly luciferase (deWet et al. (1987), Mol. Cell. Biol. 7:725–737); bacterial luciferase (Engebrecht and Silverman (1984), PNAS 1:4154–4158; Baldwin et al. (1984), Biochemistry 23:3663–3667); phycobiliproteins (especially phycoerythrin); alkaline phosphates (Toh et al. (1989) Eur. J Biochem. 182:231–238, Hall et al. (1983) J. Mol. Appl. Gen. 2:101), secreted alkaline phosphate (Cullen and Malim (1992) Methods in Enzymol. 216:362–368) or fluorescent proteins (e.g., GFP). Other examples of suitable reporter genes include those which encode proteins conferring drug/antibiotic resistance to the host mammalian cell.

The amount of transcription from the reporter gene may be measured using any suitable method. Various suitable methods are known in the art. For example, specific RNA expression may be detected using Northern blots, or specific protein product may be identified by a characteristic stain or an intrinsic activity.

In preferred embodiments, the protein encoded by the reporter is detected by an intrinsic activity associated with that protein. For instance, the reporter gene may encode a gene product that, by enzymatic activity, gives rise to a detection signal based on, fluorescence, colour, or luminescence.

In other preferred embodiments, the reporter gene provides a selection method such that cells in which the reporter gene is activated have a growth advantage. For example the reporter could enhance cell viability, e.g., by relieving a cell nutritional requirement, and/or provide resistance to a drug. Another class of useful reporter genes encode cell surface proteins for which antibodies or ligands are available. Expression of the reporter gene allows cells to be detected or affinity purified by the presence of the surface protein.

In particular embodiments, it may desirable to provide two or more reporter gene constructs which are regulated by interaction of the bait and prey proteins, e.g., GFP and BFP reporter genes. The simultaneous expression of the various reporter genes provides a means for distinguishing actual interaction of the bait and prey proteins from, e.g., mutations or other spurious events that activate the reporter gene.

The reporter gene can be maintained in the mammalian cell episomally or can be integrated into a chromosome of the mammalian cell. Preferably, the reporter gene is integrated into the chromosone of the gene.

An exemplary reporter construct is the pG5GFP.Hyg shown in FIG. 1. This plasmid can be constructed as follows. The SV40 polyadenylation signal (SmaI-MluI fragment from pGFP-C1, Clontech (Palo Alto, Calif.)) can be inserted downstream to the GFP cDNA (at Not1 site in the multiple cloning site of pEGFP, Clontech (Palo Alto, Calif.)). The CAT gene of pG5CAT reporter plasmid (Clontech, Palo Alto, Calif.) is replaced by the GFP cDNA with the SV40 polyadenylation signal, generating pG5GFP. A hygromycin resistant gene expression cassette from pCEP4 (Invitrogen, Carlsbad, Calif.) can be inserted into the Smal Site of pGFP, generating pG5GFP.hyg.

Host Cells

Any cultured mammalian cell can be used in the present mammalian two-hybrid system, e.g., a primary, secondary, or immortalized cell. Exemplary mammalian cells are those of mouse, hamster, rat, rabbit, dog, cow, and primate including human. They may be of a wide variety of tissue types, including mast cells, endothelial cells, hepatic cells, kidney cells, or other cell types.

As used herein, the term primary cell means cells isolated from a mammal (e.g., from a tissue source), which are grown in culture for the first time before subdivision and transfer to a subculture. The term secondary cell means cells at all subsequent steps in culturing. That is, the first time a plated primary cell is removed from the culture substrate and replated (passaged), it is referred to as a secondary cell, as are all cells in subsequent passages. Examples of mammalian primary and secondary cells which can be transfected include fibroblasts, keratinocytes, epithelial cells (e.g., mammary epithelial cells, intestinal epithelial cells), endothelial cells, glial cells, neural cells, formed elements of the blood (e.g., lymphocytes, bone marrow cells), muscle cells and precursors of these somatic cell types.

Immortalized cells are cell lines that exhibit an apparently unlimited lifespan in culture. Examples of immortalized human cell lines useful for the present mammlian two-hybrid system include, but are not limited to, HT1080 cells (ATCC CCL 121), HeLa cells and derivatives of HeLa cells (ATCC CCL 2, 2.1 and 2.2), MCF-7 breast cancer cells (ATCC BTH 22), K-562 leukemia cells (ATCC CCL 243), KB carcinoma cells (ATCC CCL 17), 2780AD ovarian carcinoma cells (Van der Blick, A.M. et al., Cancer Res, 48:5927–5932 (1988), Raji cells (ATCC CCL 86), Jurkat cells (ATCC TIB 152), Namalwa cells (ATCC CRL 1432), HL-60 cells (ATCC CCL 240), Daudi cells (ATCC CCL 213), RPMI 8226 cells (ATCC CCL 155), U-937 cells (ATCC CRL 1593), Bowes Melanoma cells (ATCC CRL 9607), WI-38VA13 subline 2R4 cells (ATCC CLL 75.1), and MOLT-4 cells (ATCC CRL 1582), as well as heterohybridoma cells produced by fusion of human cells and cells of another species. Secondary human fibroblast strains, such as WI-38 (ATCC CCL 75) and MRC-5 (ATCC CCL 171) may be used. In a preferred embodiment, a CV-1 cell is used.

In one aspect of the invention, the prey plasmid containing an oriP sequence is transfected into a mammalian cell expressing EBNA-1. Methods of manipulating a mammalian cell to express EBNA-1 are well known in the art. For example, the EBNA-1 sequence can be cloned into an expression vector, transfected into a mammalian cell and expressed therein. In a preferred embodiment, the mammalian cell into which the oriP prey plasmid is transfected is a mammalian cell that allows the ori-P prey plasmid to replicate episomally and indefinitely in the cell without causing cell death or transformation. Preferably, the cell is not a rodent cell. Preferably, the cell is derived from a primate or a canine.

Methods of transfecting the DNA molecules described herein (e.g., the reporter gene and associated DNA binding sites, or DNA molecules that encode EBNA-1, the bait fusion protein, or prey fusion protein) into a mammalian cell can be carried out using procedures known in the art. Examples of transfection methods include calcium phosphate or calcium chloride co-precipitation, DEAE-dextran-mediated transfection, lipofection, biolistic transfer, or electroporation. Suitable methods for transfecting host cells in vitro can be found in Sambrook et al., eds., Molecular Cloning: A Laboratory Manual (2nd ed., Cold Spring Harbor Laboratory Press, Cold Spring Harbor, N.Y., 1989) and other laboratory manuals. In a preferred embodiment, cells are transfected using LipofectAMINE PLUS reagent (Gibco/BRL, San Fran., Calif.).

Screening Assays

The present mammalian two-hybrid system can be used to screen for agents which can act as agonists or antagonists of protein-protein interactions. In a general sense, the assay evaluates the ability of an agent to modulate binding between the bait and prey polypeptides. Exemplary agents include peptides, nucleic acids, carbohydrates, small organic molecules, and natural product extract libraries, such as isolated from animals, plants, fungus and/or microbes.

In an exemplary screening assay of the present invention, the methods described herein can be used to determine if an agent of interest can modulate the binding between a bait and a prey fusion protein, which are known to interact. The ability of the agent to modulate the interaction can be determined by detecting an increase or decrease in reporter gene expression, e.g., expression of a fluorescent protein, e.g., GFP. Where a decrease in reporter gene expression in the presence of the agent of interest is detected and compared to a control cell, the agent is predicted to inhibit the interaction between the bait and prey. Alternatively, where the agent causes an increase in reporter gene expression in the presence of an agent of interest, as compared to a control cell, the agent is predicted to enhance the interaction between the bait and prey polypeptides. In the control cell, expression of the reporter gene is determined in the absence of an agent of interest.

The present invention can also be used to screen for agents which are useful for regulating gene expression in vivo. For example, an agent of interest can be tested for its ability to modulate the interaction between a DNA-binding domain and its DNA binding site, where the DNA-binding domain is known to interact with the DNA binding site.

Kit

The invention provides a kit for detecting interaction between a protein of interest and a sample protein. In an illustrative embodiment, the kit includes at least one construct and a host cell. In a preferred embodiment, the kit includes: (a) a first gene construct which includes a regulatory sequence operably linked to a nucleotide sequence encoding a DNA-binding domain, and a cloning site, (e.g., a convenient cloning site which contains a unique restriction site(s)) for inserting a nucleotide sequence which encodes a bait. The nucleotide sequence which encodes the bait is expressed in frame with a DNA-binding domain. The kit further includes: (b) a second gene construct including an oriP sequence, a regulatory sequence operably linked to a nucleotide sequence encoding a transcriptional activation domain, and a cloning site, (e.g., a convenient cloning site which contains a unique restriction site(s)) for inserting a nucleotide sequence which encodes a prey such that the prey is expressed in frame with the transcriptional activation domain; (c) a reporter gene construct which contains a sequence which encodes a fluorescent polypeptide operably linked to a transcriptional regulatory sequence including a DNA binding site for the DNA-binding domain of construct (a); (d) a mammalian cell that expresses EBNA-1 and (e) instructions for use. In a preferred embodiment, the reporter gene is integrated into the chromosome of the mammalian cell.

The kit can also include primers, which can be used to amplify the prey sequence. Optionally, the kit can also include bacterial cells into which one can introduce total DNA from a mammalian cell that was identified to contain a positive interaction between the bait and prey.

Other Uses for the Methods Described Herein

The methods described herein can be used for a variety of different purposes, e.g., for identifying protein-protein interactions, for generating protein linkage maps, for identifying therapeutic targets, and/or for general cloning strategies.

The methods can also be used to generate antibody equivalents for specific determinants, e.g., such as single chain antibodies, minibodies or the like. For example, a target polypeptide (or epitope thereof) for which an antibody or antibody equivalent is sought can be displayed on either the bait or prey fusion protein. A library of potential binding partners can be arrayed on the other fusion protein, as appropriate. Interactions between the target polypeptide and members of the library of binding partners can be detected according to methods described herein.

Alternatively, the methods described herein can be used to map residues of a protein involved in a known protein-protein interaction. Thus, for example, various forms of mutagenesis can be utilized to generate a combinatorial library of either bait or prey polypeptides, and the ability of the corresponding fusion protein to bind its partner assayed.

The present methods could be modified such that the methods could be used as a single hybrid method. For example, the method can be used to clone binding domains specific for a given nucleotide sequence, or alternatively to identify the nucleotide sequence specificity for a known DNA-binding domain.

EXAMPLE 1

Transfection of a Prey Gene into a Mammalian Cell

A cell line that showed high efficiency of transient transfection and which was found to be a useful as a mammalian host cell in the mammalian-two-hybrid system is the CV-I/EBNA-1 cell line. The CV-I/EBNA-1 is a monkey kidney cell line expressing EBNA-1 by stable transfection of its expression plasmid. This cell line can be purchased from American Type Culture Collection (ATCC). CV-1/EBNA-1 cells showed very high efficiency of transient transfection. Using LipofectAMINE PLUS reagent (Gibco/BRL, San Fran., Calif.), up to 50% of the cells were positively transfected as evaluated by transfection of a β-galactosidase expression plasmid followed by enzymatic in situ cell staining.

The CV-1/EBNA-1 cell line maintained plasmids containing the oriP episomally with almost 100% efficiency, and the copy number of the maintained plasmids was about 20 per cell. Since the oriP-plasmids were maintained episomally in a closed circular form, they were introduced into bacterial hosts. By simply transforming bacteria with total cellular DNA prepared from transfected mammalian cells, the plasmid was easily recovered in Ap-resistant bacterial colonies.

EXAMPLE 2

To Identify Positive Clones.

A Green Fluorescence reporter plasmid, pG5GFP.hyg (FIG. 1), whose transcription was activated by GAL4 DNA-binding domain fusion transcriptional activators was constructed. This reporter gene expresses green fluorescence when its reporter transcription is activated by an interaction between a bait and a prey. pG5GFP.hyg did not show significant background fluorescence in the absence of two-hybrid interactions.

A CV-1/EBNA-1 cell line that stably harbors the pG5GFP reporter integrated within the chromosomal DNA (termed the GalBright cell line) was constructed. This cell line showed green fluorescence only when GAL4 DNA-binding domain fusion proteins (baits) and transcriptional activator fusion proteins (prey) interacted within them. It was very easy to identify the positive clones under the fluorescence microscope, without damaging the cells. The green fluorescence was detected as early as 16 hours after transfection.

The green fluorescence-positive colonies were easily isolated by conventional cell cloning methods using small plastic cylinders. Isolated colonies were subcultured in separate culture dishes and the green fluorescence-positive colonies recloned until all cells growing in a culture dish showed fluorescence.

This protocol allows the isolation of two-hybrid positive clones directly and quickly without bias-prone enrichment steps or lengthy drug selection.

EXAMPLE 3
Mammalian Two-hybrid System Using GFP

As a model two-hybrid interaction, the interaction between a Smad4 C-terminal domain fragment [Smad4(C)] and a MSG1 transcriptional activator was tested. The interaction of Smad4 with MSG1 has been published (Shioda et al. PNAS, 95:9785–9790, 1998). Bait fusion proteins containing Smads of different lengths were assayed for their ability to bind a prey fusion protein containing MSG1 as follows.

The pG5GFP reporter (FIG. 1) and a GAL4 DNA-binding domain (GAL4DB) fusion MSG1 transactivator (used as a positive control) were transiently co-transfected by LipofectAMINE into CV-1/EBNA-1 cells. Strong expression of the green fluorescent protein (GFP) was observed. Transfection efficiency of this cell line by lipofection was up to 50% when evaluated by cotransfecting a β-galactosidase expression plasmid followed by in situ enzyme assay. There was no background green fluorescence when GAL4DB-MSG1 lacking the transactivation domain (the CR2 domain) or GAL4DB without fusion were transfected.

Transfection of a GAL4DB-smad4(C) (amino acids 302–552) bait did not result in background fluorescence either. As expected, cotransfection of the GAL4DB-Smad4(C) bait and MSG1 (full-length containing its intrinsic transactivation domain) resulted in strong induction of GFP expression. Note that the culture medium contained 10% fetal calf serum throughout the experiments.

When GALDB-smad4(C) was cotransfected with an MSG1 mutant lacking its Smad4-interaction domain (amino acids 30–60), no green fluorescence induced. These results demonstrated strong expression of GFP from the pG5GFP reporter only when a GAL4DB-bait and an activator-containing prey interacted. Without positive two-hybrid interactions, the background GFP expression from this reporter was negligible.

EXAMPLE 4
Construction of Stable CV-1/EBNA-1 Cell Line Containing GFP Reporter Gene CV-1/EBNA-1 cells were stably transfected with pG5GFP.Hyg (FIG. 1) and selected with hygromycin B for 2 weeks. Among about 300 hygromycin-resistant clones, a cell line that showed desirable characteristics was selected by functional two-hybrid analysis and designated "GalBright" cells. GalBright cells grew as rapidly as the parental cells.

EXAMPLE 5
GalBright Cells and the oriP Sequence

Figure 6:
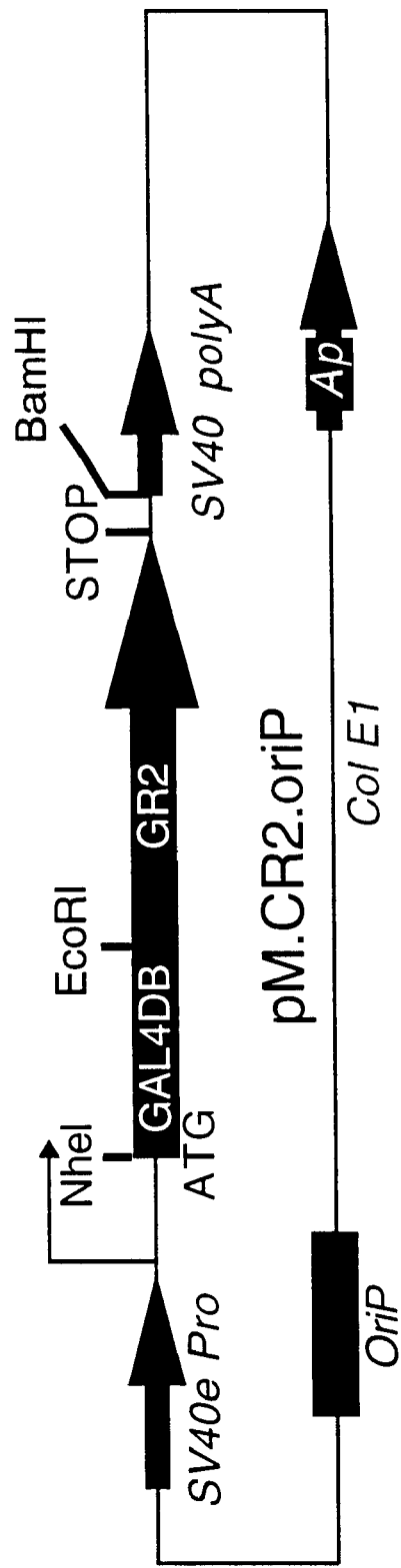
FIG. 6 is a schematic drawing of the expression plasmid, pM.CR2.oriP. Also depicted are the GAL4 DNA-binding domain (GAL4BD), the CR2 domain, SV40 early promoter (SV40e), and the selection marker ampicillin (Ap).

To determine whether GalBright cells maintain plasmids that contain the oriP sequence, oriP sequence-containing test cells were transiently transfected with expression plasmids for GAL4DB-CR2 transactivator (FIG. 6). The GLA4DB-CR2 plasmid was constructed as follows. The oriP sequence was excised from pCEP4 (AccI—AccI fragment, Invitrogen, Carlsbad, Calif.) and inserted into the pM.CR2 plasmid at an NdeI site, generating pM.CR2.oriP plasimd. Details on the pM.CR2 plasmid are published in Shioda et al., PNAS, 95:9785–9790, 1998. Control cells that did not contain the oriP sequence were similarly tranfected. At 24 hours after transfection, transfected GalBright cells showed strong green fluorescence regardless of the presence or absence of the oriP sequence in the expression plasmids. However, at one week after transfection, only those cells that had been transfected with oriP-containing expression plasmid still showed strong green fluorescence. This demonstrated that GalBright cells maintained oriP-containing plasmids for a long time and formed green fluorescent colonies that could be isolated readily from culture dishes by conventional cloning methods.

EXAMPLE 6
Mammalian Cell Two-hybrid Cloning Procedure

To isolate cDNA clones for proteins that interact with SMAD4 (bait) in mammalian cells, a bait expression plasmid is constructed by fusing cDNA for SMAD4 with GAL4 DNA-binding domain.

Protein expression of the GAL4DBD-SMAD4 is confirmed by transient transfection of the plasmid into the GalBright cells followed by Western blotting using anti-GAL4DBD antibodies, or using anti-SMAD4 antibodies.

Stably transfected GalBright cells containing the bait plasmid are selected using G418 selection. Stable clones that express the bait protein (GAL4DBD-SMAD4) are isolated by evaluating clones with Western blotting using anti-GAL4DBD and anti-SMAD4 antibodies. Several clones are isolated to ensure successful screening. The bait-expressing GalBright Cells are then transfected with prey plasmids, which contain cDNAs derived from a mouse embryo library. The prey plasmid contains the oriP sequence and is transfected into a CV-1 cell expressing EBNA-1 using LipofecAMINE Plus.

The presence of a green fluorescing cell is determined by fluorescence microscopy, using a conventional FITC filter set. Fluorescence, if present, is detected within 96 hours.

The green fluorescent GalBright cells are recovered directly by using a micropipette. In another experiment, green fluorescent GalBright cells are isolated using conventional cloning cylinders with about 0.5 cm diameter and trypsinization.

On occasion, while recovering the green fluorescent positive cells, negative surrounding cells are also recovered. When this occurs, the single cell suspension of recovered cells are inoculated into new culture dishes with low density so that they will form single-cell derived, isolated colonies. The positive clones are stored in full freezing medium at −150° C. or liquid nitrogen.

To identify the sequence that encodes the prey plasmid, the total DNA from the positive GalBright cells is prepared using standard methods. At this point two alternative procedures are used to isolate the interactor protein.

In the first procedure, bacteria are transformed with total cellular DNA preparation. Transformed bacterial clones are plated on LB-Ap plates overnight. Bacterial plasmid DNAs are recovered using a standard plasmid miniprep method.

Since GalBright cells can harbor more than one species of the prey library plasmid, 10 or more bacterial colonies are reovered and plasmid DNA is prepared.

The recovered plasmid DNA is then reintroduced into the bait-expressing GalBright cells and non-expressing GalBright cells. True prey plasmid give green fluorescence only for the bait-expressing GalBright cells by the two-hybrid interaction, but not for the non-expressing cells. In some cases where the non-expressing cells show green fluorescence, the prey is a nonspecific transcriptional activator that activates the reporter gene of the Gal Bright cells independent of the bait. Prey plasmids are characterized by amplifying the prey sequence by PCR, using primers designed on the vector sequences.

In the second procedure, the total DNA from positive (fluorescent) cells is isolated. The identity of the sequence that encodes the prey protein is determined by conventional PCR and sequence analysis Other embodiments are within the following claims.

What is claimed is:

1. A method for detecting interaction between a bait and a prey in a mammalian cell two hybrid system, comprising:
    (a) providing a mammalian cell comprising: a reporter gene encoding a fluorescent polypeptide operably linked to an upstream transcriptional regulatory sequence comprising a DNA binding site for a DNA-binding domain, the reporter gene and transcriptional regulatory sequence being integrated into a chromosome of the mammalian cell;
    (b) introducing into the cell a DNA molecule comprising a first nucleotide sequence encoding a bait fusion protein, comprising an upstream GAL4 DNA-binding domain and the bait;
    (c) introducing into the cell a DNA molecule comprising a nucleotide sequence encoding prey fusion protein comprising an upstream transcriptional activation domain and the prey, the transcriptional activation domain being selected from the group consisting of a GAL4 transcriptional activation domain, a VP16 transcriptional activation domain, and a CR2 transcriptional activation domain from MSG1;
    (d) incubating the cell for 96 hours or less;
    (e) detecting reporter gene expression, if present, thereby detecting interaction between the bait and the prey.

2. The method of claim 1, further comprising isolating DNA from a cell expressing the reporter gene, and amplifying the nucleotide sequence from steps (b) and (c) of claim 1.

3. The method of claim 1, wherein the cell is an immortalized cell.

4. The method of claim 1, wherein the cell is a CV-1 cell.

5. The method of claim 1, wherein the fluorescent polypeptide is a green fluorescent protein (GFP) or a blue fluorescent protein (BFP).

6. The method of claim 1, wherein the bait or prey is encoded by a nucleotide sequence from a nucleic acid library.

7. A kit for detecting interaction between a bait and a prey in a mammalian cell, comprising:
    (a) a first gene construct comprising:
        a regulatory sequence operably linked to a nucleotide sequence encoding a DNA-binding domain, and
        a cloning site for inserting a nucleotide sequence encoding the bait into the first gene construct such that the bait is expressed in frame with the DNA-binding domain;
    (b) a second gene construct containing an oriP sequence comprising:
        a regulatory sequence operably linked to a nucleotide sequence encoding a transcriptional activation domain, and
        a cloning site for inserting a nucleotide sequence encoding the prey into the second gene construct such that the prey is expressed in frame with the transcriptional activation domain; and
    (c) a mammalian cell that expresses an EBNA-1, comprising a reporter gene encoding a fluorescent polypeptide operably linked to a transcriptional regulatory sequence including a DNA binding site for the DNA-binding domain, wherein the reporter gene expresses the fluorescent polypeptide when the bait and prey interact; and
    (d) instructions for use.

* * * * *